United States Patent [19]

Mizuno et al.

[11] Patent Number: 4,459,198
[45] Date of Patent: Jul. 10, 1984

[54] ELECTROPHORETIC APPARATUS

[75] Inventors: Toshie Mizuno, Takatsuki; Shoichi Kobayashi, Nagaokakyo, both of Japan

[73] Assignee: Shimadzu Corporation, Kyoto, Japan

[21] Appl. No.: 361,738

[22] Filed: Mar. 23, 1982

[30] Foreign Application Priority Data

| Jul. 27, 1981 [JP] | Japan | 56-118053 |
| Jul. 27, 1981 [JP] | Japan | 56-118054 |
| Jul. 27, 1981 [JP] | Japan | 56-118056 |
| Oct. 31, 1981 [JP] | Japan | 56-176112 |

[51] Int. Cl.³ .................. G01N 27/28; G01N 27/26
[52] U.S. Cl. ........................... 204/299 R; 204/180 R
[58] Field of Search ............ 204/180 R, 299 R, 180 G

[56] References Cited

U.S. PATENT DOCUMENTS

| 3,869,365 | 3/1975 | Sunden | 204/299 R |
| 3,932,264 | 1/1976 | Haruki et al. | 204/299 R |
| 3,941,678 | 3/1976 | Akiyama et al. | 204/299 R |
| 3,998,719 | 12/1976 | Deml et al. | 204/299 R |

Primary Examiner—Winston A. Douglas
Assistant Examiner—B. J. Boggs, Jr.
Attorney, Agent, or Firm—Hubbell, Cohen, Stiefel & Gross

[57] ABSTRACT

An electrophoretic apparatus which is equipped with means for detecting that a zone of a certain kind of ion component passes through a predetermined position of a migration tube so that the electrophoresis is divided into two stages to effect a pre-separation, i.e., a rough separation of target components and to effect a fine separation for finely separating said target component and so that the switch from the pre-separation to the fine separation in automatically effected in accordance with the output of the aforementioned passage detecting means, which can shorten an analysis time and ensure a precise quantitative or qualitative analysis.

12 Claims, 28 Drawing Figures

FIG. 8
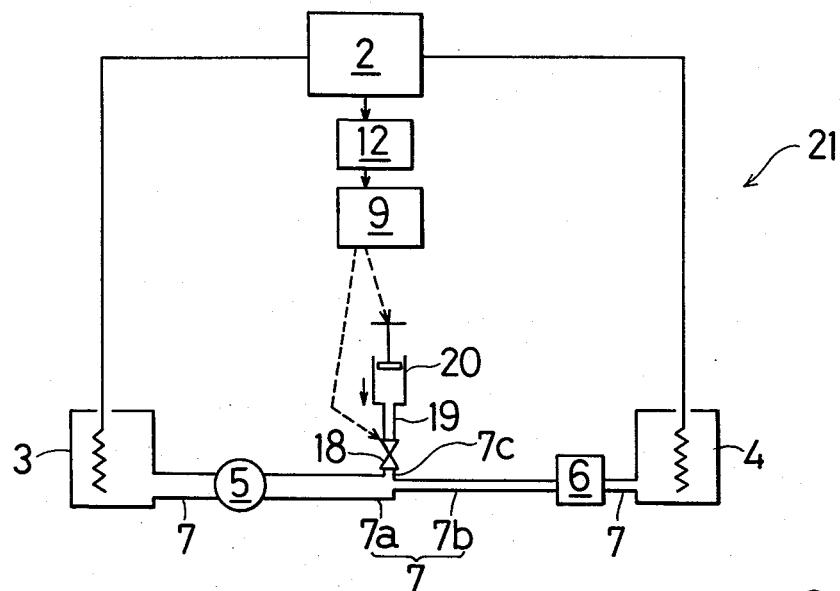
FIG. 10
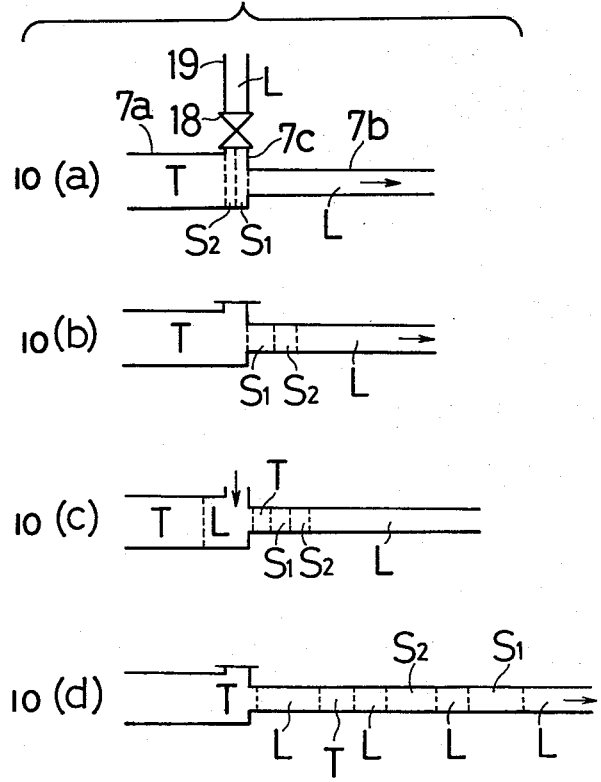
FIG. 9
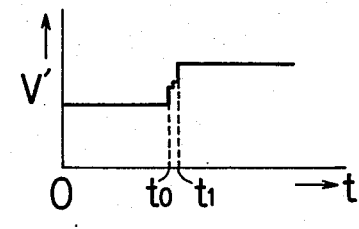
FIG. 11
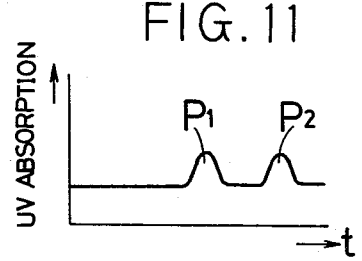
FIG. 12

ELECTROPHORETIC APPARATUS

BACKGROUND OF THE INVENTION

1. Field of the Invention

The present invention relates to an electrophoretic apparatus of the type, in which terminal and leading electrolyte chambers are connected to both the terminals of a D.C. high voltage power source circuit, respectively, a migration tube is connected between those electrolyte chambers and a sample injector and a detector are connected in this order in the migration tube.

2. Description of the Prior Art

An isotachophoresis is conducted by charging the inside of a migration tube with two kinds of electrolytes, i.e., terminal and leading electrolytes and by injecting a sample of chargeable substances such as amino acids, peptides or biological substances into the boundary between those two electrolytes to effect the electrophoresis in a constant current so that the substances to be detected may be separated in accordance with differences in their mobilities and may be qualitatively and/or quantitatively analyzed by means of a suitable detector. The isotachophoresis is therefore indispensable for the analysis of a small quantity of sample. More specifically, there is recently proposed in U.S. Pat. Nos. 3,932,264 or 3,941,678 a capillary type isotachophoretic apparatus which uses a capillary tube as a migration tube.

In such cases where the quantity of the sample is remarkably small or where the sample contains two kinds of components having remarkably near mobilities, the analysis cannot be sufficiently conducted by the electrophoretic apparatus according to the prior art. In the former case, more specifically the sample has its obtainable ion component zone so narrowed that it cannot be sufficiently detected. In the latter case, the ion component zones of the two kinds are so close to each other that they cannot be discriminated. If the migration tube is elongated, the analyzability may naturally be improved, which cannot be said to be practical in view of the analyzing efficiency.

On the other hand, in case the sample is brine and has its components in small quantities to be analyzed, the brine itself has many chloride ions which have a large mobility. According to the electrophoretic apparatus of the prior art, therefore, the chloride ion components will be detected for a long time before the target components in the small quantities are detected. This means, in other words, that a useless time period for the analysis is wasted.

In order to solve those problems and to achieve the two objects of shortening the analysis time and ensuring the precise detection, there has been proposed method, in one of which migration current is enlarged at the initial stage of the analysis to enlarge the migration velocity of the ions thereby to shorten the time period required and is reduced at the final stage of the analysis to depress generation of Joule heat thereby to ensure the precise detection. It is important in that method proposed to make proper the timing at which the migration current is to be switched. For this purpose, it is required to detect that the front edge of a predetermined ion component zone of the sample has passed through a predetermined position of a migration tube. As this detecting means, there may be conceived to dispose a detector at the predetermined position of the migration tube separately of the intrinsic detector. In this case, however, since the additional detector has to be disposed in the migration tube, the apparatus is complicated as a whole, and there arises a fear that an interaction between that detector and the sample takes place.

SUMMARY OF THE INVENTION

We, the Inventors, have earnestly endeavored investigations in view of the background thus far described and have succeeded in developing an electrophoretic apparatus which has freed of any of the aforementioned problems.

According to the present invention, in short, there is provided an electrophoretic apparatus which is equipped with a passage detecting means for detecting that a boundary between ion component zones passes through a predetermined position of a migration tube so that the electrophoresis is divided into two stages to effect a preseparation, i.e., a rough separation for roughly separating target components at the first stage of the electrophoresis and to effect a fine separation for finely separating the target components at the second stage, and a control means for converting the pre-separation to the fine separation which is automatically effected in accordance with the output of the aforementioned passage detecting means.

The combination of the pre-separation and fine separation may be specifically achieved by changing the migration current from a large current to a small current, or changing the usual isotachophoresis using leading and terminal electrolytes to a kind of zone electrophoresis using either one of said two electrolytes or another electrolyte.

Thus, according to the present invention, there is provided an electrophoretic apparatus of the type, in which a sample injector and a detector are connected in this order by means of a migration tube between terminal and leading electrolyte chambers connected with both the output terminals of a D.C. high voltage power source circuit, respectively, said electrophoretic apparatus comprising; a passage detecting means disposed in said power source circuit for detecting that a boundary between ion component zones passes through a predetermined position of said migration tube between said sample injector and said detector; and a control means for changing the output voltage and/or output current of said power source circuit in accordance with the output signal of said passage detecting means, whereby a pre-separation and a subsequent fine separation can be effected in the migration tube.

According to another aspect of the present invention, there is provided an electrophoretic apparatus of the type, in which a sample injector and a detector are connected in this order by means of a migration tube between terminal and leading electrolyte chambers connected with both the output terminals of a D.C. high voltage power source circuit, respectively, said electrophoretic apparatus comprising; a passage detecting means disposed in said power source circuit for detecting that a boundary between ion component zones passes through a predetermined position of said migration tube between said sample injector and said detector; a branch tube connected with a tube portion in the vicinity of said predetermined position; an electrolyte injection means connected with said branch tube; and a control means for operating said electrolyte injection means in accordance with the output signal of said passage detecting means, whereby a pre-separation can be effected in the migration tube by using both said leading and terminal electrolytes, and a subsequent fine separation can be effected in said migration tube by using either one of said two electrolytes or another electrolyte.

As a further aspect of the invention, there is also provided an electrophoretic apparatus of the type, in which a sample injector and a detector are connected in this order by means of a migration tube between terminal and leading electrolyte chambers connected with both the output terminals of a D.C. high voltage power source circuit, respectively, said electrophoretic apparatus comprising: a passage detecting means disposed in said power source circuit for detecting that a boundary between ion component zones passes through a predetermined position of said migration tube between said sample injector and said detector; a switching connection means disposed in said predetermined position and having a communication path for migration and another communication path for electrolyte injection, arbitrary one of which is switched to be connected with said migration tube; and a control means for switching said switching connection means in accordance with the output signal of said passage detecting means, whereby a pre-separation can be effected in the migration tube by using both said leading and terminal electrolytes, and a subsequent fine separation can be effected in said migration tube by using either one of said two electrolytes or another electrolyte.

The aforementioned "predetermined position" means a position which exists actually or notionally in the migration tube between the sample injector and the detector and which can be theoretically determined as a distance from the sample injector position depending upon a diameter of the migration tube and so forth. It would be a position where the separations of components come to an end in the rough sense of the word, which means the preservation of a certain disturbance of the boundary caused by the higher current and so forth. On the other hand, the distance between "predetermined position" and the detector would be determined empirically so long as to eliminate the disturbance caused by the rough separation without much loss.

An example of the aforementioned passage detecting means disposed in the power source circuit comprises: a current detecting means for detecting the migration current which is supplied from said power source circut; a current integrating means for timewise integrating the currents detected; and a comparison means for comparing the integrated value with a predetermined threshold value. In an alternative example, the passage detecting means comprises: a voltage change measuring means connected with said power source circuit for measuring the timewise change in the voltage supplied; and a comparison means for comparing the change in the voltage measured with a predetermined threshold value. In the latter case, the migration tube is preferred to be formed with an abruptly diameter-varying portion at the predetermined position, because the change in the voltage becomes so unique that it can be easily detected.

BRIEF DESCRIPTION OF THE DRAWINGS

FIG. 6(I) is a schematic view illustrating ion component zones during a blank operation; FIG. 6(III) is a chart illustrating the output signal of a detector;

FIG. 7(I) is a schematic view illustrating the ion component zones when a sample is injected.

FIG. 8 is a diagram showing the construction of an electrophoretic apparatus according to a further embodiment of the present invention;

FIG. 9 is a chart illustrating the timewise changes in the first order derivative of the voltage supplied when the isotachophoresis is conducted by the use of the apparatus of FIG. 8;

FIG. 10 is an explanatory view illustrating the proceedings of the migration state when the electrophoresis is conducted by the use of the apparatus of FIG. 8;

FIG. 11 is a chart illustrating the data which are obtained by the use of the apparatus of FIG. 8;

FIG. 12 is a chart illustrating the data which are obtained by the usual isotachophoresis;

DESCRIPTION OF THE PREFERRED EMBODIMENTS

Figure 1:
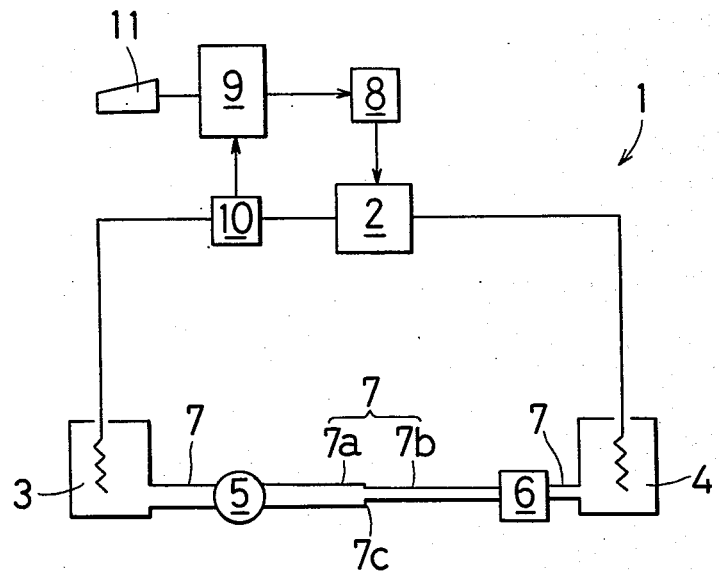
FIG. 1 is a diagram showing the construction of an electrophoretic apparatus according to one embodiment of the present invention.

In the one embodiment of the present invention shown in FIG. 1, reference numeral 1 indicates a capillary type isotachophoretic analyzing apparatus, in which terminal and leading electrolyte chambers 3 and 4 are connected with both the terminals of a D.C. high voltage power source circuit 2 and in which a sample injector 5 and a detector 6 are connected by means of a tube 7 between those two electrolyte chambers 3 and 4. The tube 7 between the sample injector 5 and the detector 6 is a two-step tube in which a first separation tube 7a having a larger diameter of 0.8 to 1.2 mm and a second separation tube (a capillary tube) 7b having a smaller diameter of 0.1 to 0.5 mm are connected in series through a stepped portion 7c. The output of the power source circuit 2 is controlled through a control circuit (change means) 8 by the operation of a microcomputer 9. Numeral 10 indicates a current detecting circuit which is connected between the power source circuit 2 and the terminal electrolyte chamber 3 and the output of which is fed to the microcomputer 9. Numeral 11 indicates a control table.

In this apparatus 1, the stepped portion 7c corresponds to a predetermined position, and, the current detecting circuit 10 and the microcomputer 9 constitute a passage detecting means.

Now, in the case of the apparatus 1 having its migration tube constructed of the two-step tube, a high migration current may be supplied when ions having a high mobility (e.g., the leading electrolyte ions) exist in the capillary tube 7b. However, if the high current is still supplied when ions having a lower mobility (e.g., the ions composing a sample) enter the capillary tube 7b, as the resistance is raised due to the diminishment in the diameter of the tube, which causes disadvantages that the supply voltage is abnormally raised, the Joule heat generated is increased and bubbles are formed in the capillary tube 7b by the heat. In spite of this fact, if a low migration current is supplied from the beginning, the migration time will be elongated. It is, therefore, desired that a migration current is set at a high value in case the ions having the low mobility exist in the first separation tube 7a and that the current is switched to a low value when those ions migrate into the capillary tube 7b. Therefore, it is usually preferred to supply a high current while the ion component zones of the sample are migrating within the first separation tube 7a and a low current while the ion component zones of the sample are migrating within the capillary tube 7b so that the time period for the analysis may be shortened and so that the detection may be precisely conducted. Thus, it is desired to catch the time when the front edge of the ion component zones of the sample reaches the stepped portion 7c and to switch the migration current from the high value to the low value at that particular time.

As is well known in the art, on the other hand, the quantity of electricity supplied during the electrophoresis is in direct proportion to the migration distance of one ion component zone. This migration distance can therefore be known by determining the quantity of electricity. Now, if the ion component zone of the leading electrolyte is noted, the relationship between that migration distance and the quantity of electricity is determined exclusively by the composition of the leading electrolyte. However, since the back edge of the ion component zone of the leading electrolyte is nothing but the front edge of the ion component zones of the sample, the migration of this front edge can be known from the relationship between the migration distance of the ion component zone of the leading electrolyte and the quantity of electricity. That is to say, so long the leading electrolyte is identical, the migration distance of the front edge of the ion component zones of the sample can be deduced from the quantity of electricity while taking none of the composition and quantity of the sample into consideration. On the other hand, if the migration currents are measured and integrated, this integrated value is just nothing but the aforementioned quantity of electricity. It therefore follows that the migration of the leading end of the ion component zones of the sample to the stepped portion can be accurately known from that integrated value.

Thus, in the apparatus 1 under consideration, composition of the leading electrolyte is made in advance to correspond to the quantity of electricity, which is required for the back edge of the ion component zone of the leading electrolyte to migrate from the sample injector 5 to the stepped portion 7c and the resultant correspondence is stored in the microcomputer 9.

Upon the analysis, the composition of the leading electrolyte is first fed through the control table 11 to the microcomputer 9. Then, this microcomputer 9 reads the quantity of electricity Q corresponding thereto out of the memory and internally sets it as a threshold value.

Next, the boundary between the terminal electrolyte and the leading electrolyte is formed in the sample injector 5 by the usual procedures, and the sample is injected. Then, a start command is introduced from the control table 11. In response to this command, the microcomputer 9 controls the power source circuit 2 through the control circuit 8 thereby to supply a relatively large migration current $i_1$ (e.g., at 200 to 300 $\mu A$). This migration current $i_1$ is fed back to the microcomputer 9 by the action of the current detecting circuit 10. The microcomputer 9 timewise integrates that migration current $i_1$ and compares a quantity of electricity q, which is obtained by that integration, with the threshold value, i.e., the aforementioned quantity of electricity Q thereby to switch the migration current $i_1$ to a relatively small migration current $i_2$ (e.g., at 20 to 100 $\mu A$) when the coincidence takes place. This coincidence between the two quantities of electricity q and Q takes place when the back edge of the ion compartment zone of the leading electrolyte comes to the stepped portion 7c, namely, when the front edge of the ion component zones of the sample reaches the stepped portion 7c.

Thus, the sample first migrates within the first separation tube 7a in the large migration current $i_1$ and then within the capillary tube 7b in the small migration current $i_2$. Moreover, these migrations are accurately effected irrespective of the composition and quantity of the sample.

The apparatus 1 thus far described may be so modified as to use an integrator incorporating an operation amplifier as the integrating means for the migration currents. Moreover, a comparator IC may also be used as the comparison means for comparing the integrated value and the threshold value.

As has already been understood from the description thus far made, according to the apparatus 1, it can be accurately detected by knowing the integrated value of the migration currents without taking any of the composition and quantity of the sample into consideration that the front edge of the ion component zones of the sample has reached the predetermined position of the migration tube, whereby the pre-separation can be accurately switched to the fine separation. Therefore, the apparatus 1 of the present invention is remarkably useful for the analysis of an unknown sample. Moreover, since only the integrated value but not the momentary value of the migration current is taken into consideration, there can be attained an advantage that the aforementioned switching operation can be conducted in either case whichever the migration current might be a constant current or a momentarily changing current.

Figure 2:
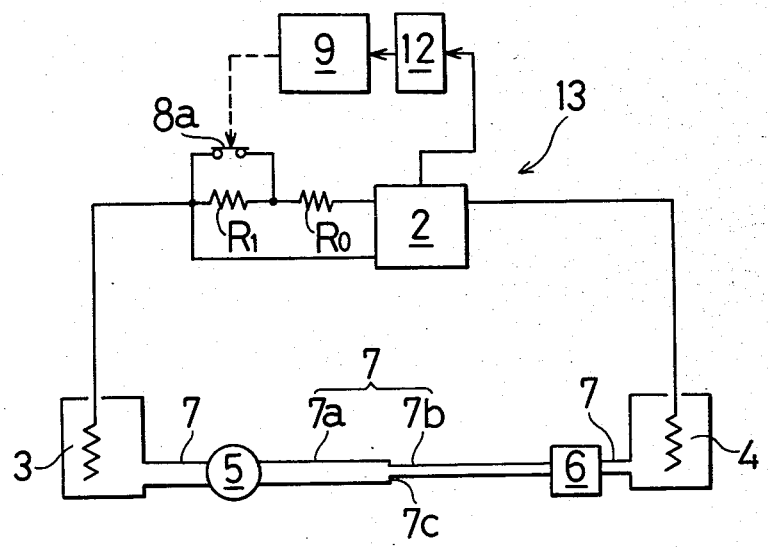
FIG. 2 is a diagram showing the construction of an electrophoretic apparatus according to another embodiment of the present invention.

FIG. 2 shows another embodiment of the electrophoretic apparatus according to the present invention wherein the numerals 2-7 represent the same meanings with those of FIG. 1.

The power source circuit 2, however has an additional means of current limiting resistors $R_0$ and $R_1$ connected in series so that it supplies a constant current by keeping the voltage drop thereat constant.

Reference numeral 12 indicates an A-D converter by which the voltage supplied from the power source circuit 2 is converted into a digital value and is fed to the microcomputer 9. This microcomputer 9 samples the A-D converter 12 at each predetermined short time interval in accordance with the operation of a built-in clock and subtracts the value upon the previous sampling operation from the sampled value. The difference thus deduced is the timewise change of the supply voltage. Therefore, the A-D converter 12 and microcomputer 9 constitute together voltage change measuring means.

Also, as stated hereinafter, the microcomputer 9 acts as comparison means for comparing the change in the voltage measured with a predetermined threshold value. Thus the microcomputer 9 constitutes the passage detecting means together with the A-D converter 12.

The microcomputer 9 further subtracts the difference, which has been deduced by the previous subtraction, from the aforementioned difference. When the difference thus doubly subtracted exceeds the predetermined threshold value, the microcomputer 9 feeds a relay 8a with an opening signal. The contacts of the relay 8a are held closed from the start of the electrophoresis to the time when the aforementioned opening signal is given thereby to short-circuit the aforementioned current limiting resistor $R_1$ and is opened in response to the opening signal. The power source circuit 2 operates to keep constant the voltage drop at the current limiting resistors $R_0$ and $R_1$, as has been described hereinbefore. Therefore, if these current limiting resistors $R_0$ and $R_1$ are assumed to have an identical resistance, the power source circuit 2 will supply a current in a half value as large as that for the closed contacts of the relay 8a when these contacts are opened. If a current of 200 $\mu$A is supplied when the contacts of the relay 8a are closed, for example, a current of 100 $\mu$A is supplied after the contacts of the relay 8a are opened. Thus, the microcomputer 9 and the relay 8a constitute together control means or change means.

The operating principle of the electrophoretic apparatus 13 for detecting that the front edge of the ion component zones of the sample passes through the stepped portion 7c will be described hereinafter.

Figure 4:
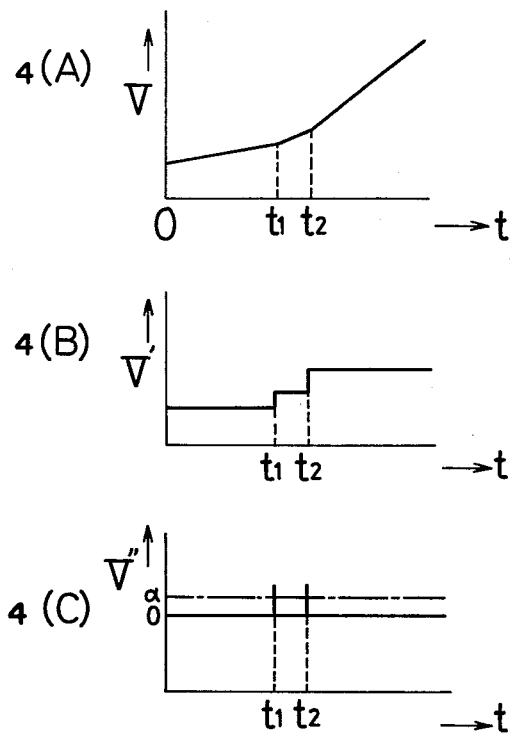
FIG. 4(A) is a chart illustrating the timewise change in the voltage supplied.
FIG. 4(B) is a chart illustrating the timewise change in the first order derivative of the same.
FIG. 4(C) is a chart illustrating the timewise change in the second order derivative of the same.

For convenience of explanation, the sample is composed only one kind of ion component zone, and the electric conductivity is reduced in the order of the zone L of the leading electrolyte→the zone S of the sample→ the zone T of the terminal electrolyte. On the other hand, the value to be handled by the microcomputer 9 is a digital value but is expressed in an analog quantity for convenience of explanation, as shown in FIG. 4. Specifically, the difference or the timewise change of the aforementioned supply voltage is expressed as a first order derivative V' of a supply voltage V, and the aforementioned difference doubly subtracted is expressed as a second order derivative V". It will be apparent that this replacement will lead to no substantial change.

Now, if the electrophoresis is conducted in a constant current, it proceeds in the order of FIGS. 3(a), (b), (c) and (d). Then, if the current values are not switched, the supply voltage V is varied in the manner shown in FIG. 4(A). Here, a time $t_1$ corresponds to the instant of FIG. 3(b), and a time $t_2$ corresponds to the instant of FIG. 3(c). As a result, the timewise change of the supply voltage V follows the first order derivative V' shown in FIG. 4(B). Moreover, the second order derivative V" is illustrated in FIG. 4(C). Thus, if a threshold value $\alpha$ is set for the value of the second order derivative V", the times $t_1$ and $t_2$ can be detected with remarkable ease.

Figure 3:
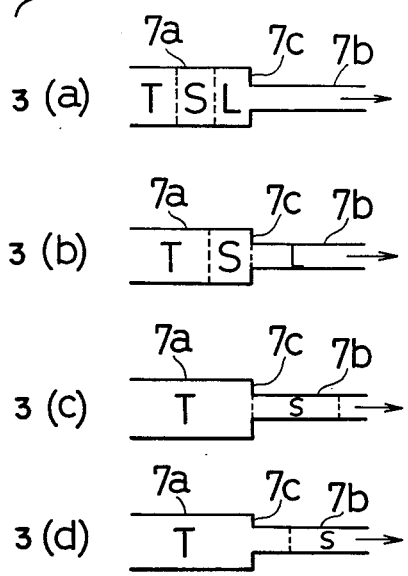
FIG. 3 is an explanatory view illustrating the proceedings of electrophoresis.

Not limited to the example shown in FIGS. 3 and 4, generally, the change of the supply voltage never fails to be a unique one when the boundary of different ion component zones passes through an abruptly diameter-varying portion of the migration tube such as the stepped portion 7c. In other words, the change of the supply voltage is a steady one when one ion component zone passes through the abruptly diameter-varying portion of the migration tube. Therefore, if the timewise change of the supply voltage is measured, the passage of a boundary of two ion component zones can be detected.

Thus, according to the electrophoretic apparatus 13, it can be accurately and easily known that each electrophoretic zone passed through the stepped portion 7c. Consequently, the switching operation is effected to the most proper current value at the most proper timing and accordingly from the pre-separation to the fine separation so that the remarkably suitable electrophoretic analysis can be conducted. Moreover, the construction can be made relatively easily.

The apparatus 13 may be modified such that the microcomputer 9 is programmed to switch the current at the time $t_2$ if the conductivity of the ion component zone S is so close to that of the leading electrolyte ion zone L that it raises no special problem in the capillary tube 7b. Moreover, an analog differentiation circuit may be used as the voltage change measuring means.

In this aforementioned passage detecting means resorting the voltage change, incidentally, it is desired that the abruptly diameter-varying portion is formed in the passage detecting position of the migration tube 7. Therefore, in case the passage is to be detected at a position other than the stepped portion 7c, it is preferable that a constructed portion having a reduced diameter or a bulging portion having a enlarged diameter is disposed at that position of the migration tube.

Figure 5:
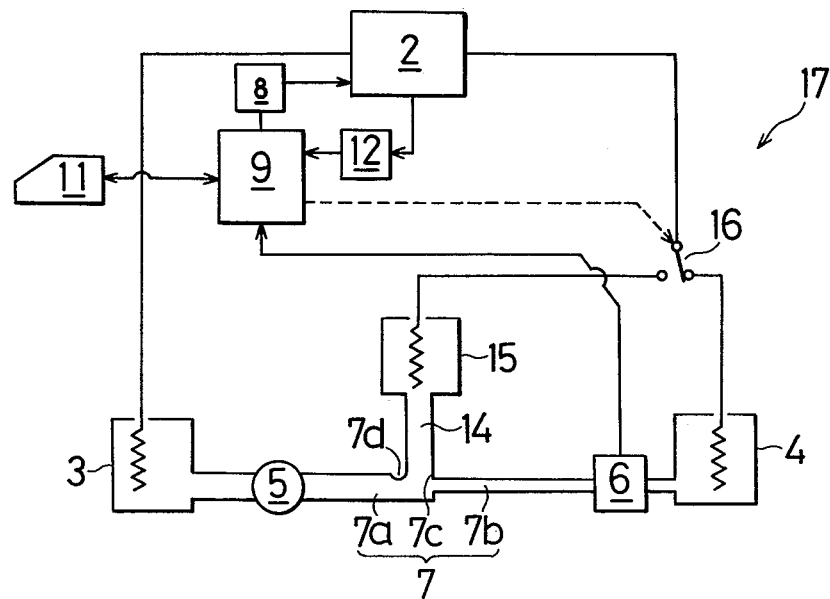
FIG. 5 is a diagram showing the construction of an electrophoretic apparatus according to a further embodiment of the present invention.

Reference numeral 17 appearing in FIG. 5 shows a further embodiment of the electrophoretic apparatus according to the present invention. The power supply circuit 2 has its one terminal connected with the terminal electrolyte chamber 3 and its other terminal connected through a switching circuit 16 with the first leading electrolyte chamber 4 and a second leading electrolyte chamber 15.

Those chambers 3, 4 and 15 are connected by means of the tube, and the sample injector 5 and the potential gradient detector 6 are disposed in this order in the tube between the terminal electrolyte chamber 3 and the first leading electrolyte chamber 4.

The tube between the sample injector 5 and the detector 6 is the two-step tube 7 in which the first separation tube 7a having a larger diameter (e.g., 1 mm) and the capillary tube 7b having a smaller diameter (e.g., 0.3 mm) are connected in series through the stepped portion 7c. The tube 14 to the second leading electrolyte chamber 15 is branched from just upstream of the aforementioned stepped portion 7c. That tube 14 is made to have the same diameter as that of the aforementioned first separation tube 7a. The portion of the tube 7a just upstream of the branch of the tube 14 is formed with a constricted portion 7d as the abruptly diameter-varying portion.

In a way similar to the apparatus 13, the A-D converter 12 and the microcomputer 9 constitute together passage detecting means for generating an output when the boundary of ion component zones having different mobilities passes through the aforementioned constricted portion 7d which corresponds to the predetermined position.

On the other hand, the switching circuit 16, and the change circuit 8 constitute together the control means.

Figure 6:
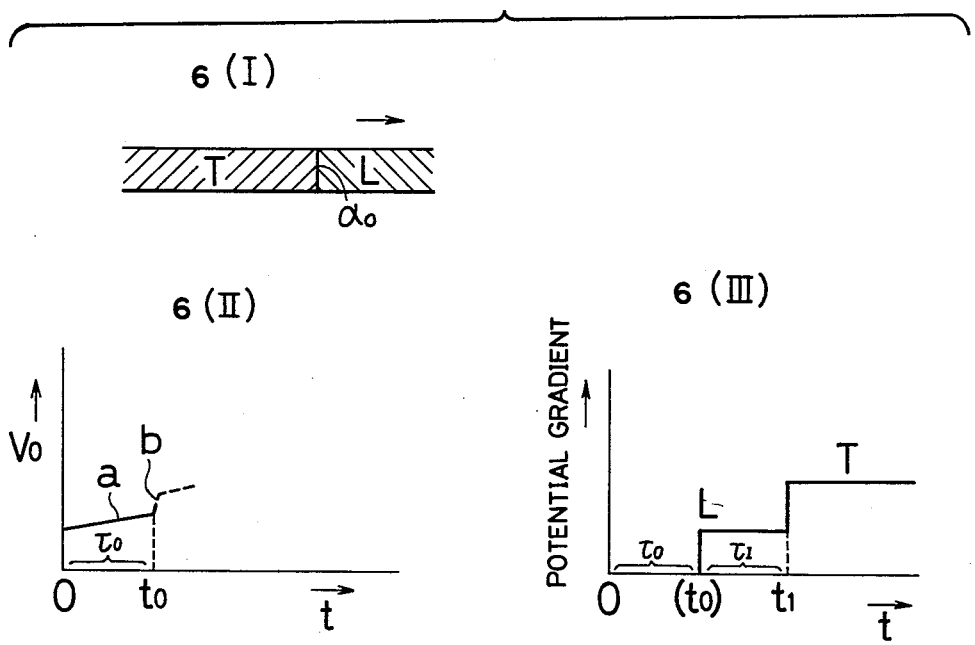
FIG. 6(II) is a chart illustrating the timewise change in the voltage supplied.

In the electrophoretic apparatus 17 thus constructed, first of all, the boundary between the terminal and leading electrolytes is formed in the sample injector 5 by the usual procedures, and a command "blank start" is fed from the control table 11 without any injection of the sample, i.e., in a blank manner. In response to this command, the microcomputer 9 controls the power source circuit 2 and the switching circuit 16 to supply a constant current $I_1$ (e.g., at a value of 200 to 300 μA) between the terminal electrolyte chamber 3 and the second leading electrolyte chamber 15. If the constant current $I_1$ is held as it is, moreover, the leading electrolyte ion component zone L and the terminal electrolyte ion component zone T are subjected to the isotachophoresis between the chamber 3 and 15, as shown in FIG. 6. At this time, the supply voltage $V_0$ from the power source circuit 2 is raised, as shown in FIG. 6(II), but the rising gradient exhibits a unique change when the back edge $\alpha_0$ of the leading electrolyte ion component zone L passes through the constricted portion 7d, as indicated at letters a and b. Then, the microcomputer 9 monitoring the supply voltage $V_0$ through the A-D converter 12 instantly detects the time $t_0$ when the boundary $\alpha_0$ passes through the constricted portion 7d from the change in the rising gradient of the supply voltage $V_0$. Moreover, the microcomputer 9 stores that time $t_0$ and controls the power source circuit 2 and the switching circuit 16 to supply a constant current $I_2$ (e.g., at a value of 20 to 100 A) between the terminal electrolyte chamber 3 and the first leading electrolyte chamber 4. One of the reasons why the current is reduced is because the low level of the conductivity of the terminal electrolyte will excessively increase the Joule heat and raise the supply voltage $V_0$ if the constant current $I_1$ is held at the high value. The leading electrolyte ion component zone L and the terminal electrolyte ion component zone T will continue the isotachophoresis in the constant current $I_2$ until the detector 7 generates such a signal as is shown in FIG. 6(III). Thus, the microcomputer 9 detects and stores the time $t_1$ when the boundary $\alpha$ arrives at the detector 6. If the start time of the electrophoresis is assumed to be 0, the aforementioned time $t_0$ is nothing but the period $\tau_0$ for which the back edge $\alpha_0$ of the leading electrolyte ion component zone L migrates in the constant current $I_1$ from the sample injector 5 to the constricted portion 7d, and the aforementioned time $t_1$ is nothing but the sum of the aforementioned period $\tau_0$ and the period $\tau_1$ for which the boundary $\alpha_0$ migrates in the constant current $I_2$ from the constricted portion 7d to the detector 6.

Figure 7:
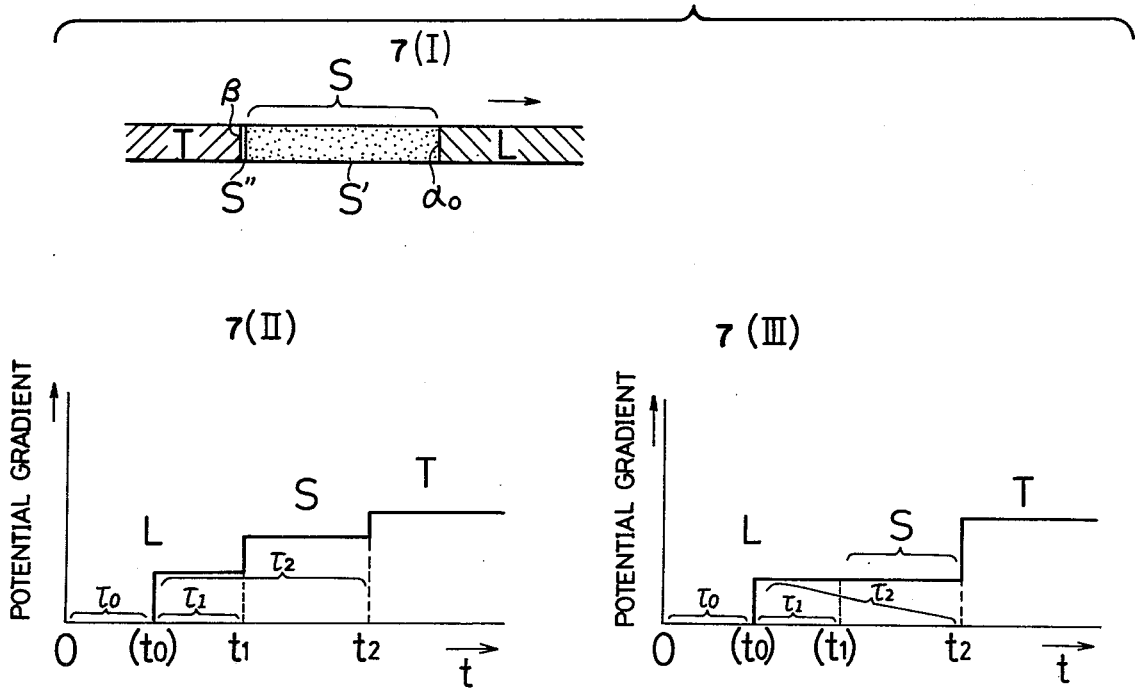
FIGS. 7(II) and 7(III) are charts illustrating the output signals of the detector.

Next, in the electrophoretic apparatus 17 being considered, there is formed in the sample injector 5 by the usual procedures the boundary between the terminal and leading electrolytes, into which a sample in a quantity of one nth of a conventional quantity is injected. More specifically, it is assumed that the sample is urine and that the detection of components contained therein requires injection of urine of 1 μl in a conventional case. Then, urine in a quantity of 0.1 μl, which is one tenth of said conventional value 1 μl, or a sample of 1 μl, which is ten times diluted with the terminal electrolyte, is injected. Then, operator provides through the control table 11 a command "start of one nth". In response to this command, the microcomputer 9 supplies the constant current $I_1$ between the chambers 3 and 15 similarly to the operation of the "blank start" but effects the switching operation to the supply of the constant current $I_2$ between the chambers 3 and 4 after the supply of the time $t_0$ which has been stored before. The detector 6 obtains such a signal by the electrophoresis as is illustrated in FIG. 7(II) or (III). Here, capital letter S indicates the ion component zone of the sample, which is composed mostly of a zone S' of a component having a relatively high mobility and other than a target component. A zone S" of the target component in a small quantity exists in a small length but is so short that it is hardly detected. If the conductivity of the ion component zone S' of the component other than the target is apparently lower than that of the leading electrolyte ion component zone S, that signal becomes that illustrated in FIG. 7(II). However, this signal becomes that illustrated in FIG. 7(III) if that conductivity is about or equal to that of the ion component zone L. In response to the output signal of the detector 6, the microcomputer 9 detects and stores the time $t_2$ when the leading end boundary $\beta$ of the terminal electrolyte ion component zone T reaches the detector 6. This time $t_2$ is nothing but the sum of the aforementioned period $\tau_0$ and the period $\tau_2$ from the instant when the supply of the constant current $I_2$ is started to the instant when the detector 6 detects the boundary $\beta$. The microcomputer 9 then conducts the calculation of the following Equations by the use of a suitable safety factor C (e.g., at a value of 0.95) which is fed in advance from the control table 11 while having a value smaller than 1:

$$\tau_0 = t_0 \qquad (1);$$

$$\tau_3 = (t_2 - t_1) \times n \times (I_2/I_1) \qquad (2);$$

and $$\tau = C \times (\tau_0 + \tau_3) \qquad (3).$$

Next, in the electrophoretic apparatus 17 thus constructed, there is formed in the sample injector 5 by the usual procedures the boundary between the terminal and leading electrolytes, into which a sample in a conventional quantity (e.g., urine of 1 μl) is injected. A command "measurement start" is introduced from the control table 11. Then, the microcomputer 9 controls the power source circuit 2 and the switching circuit 16 to supply the constant current $I_1$ between the terminal electrolyte chamber 3 and the second leading electrolyte chamber 15 for the time period $\tau$. This time period $\tau$ is slightly shorter than the sum of the time periods $\tau_0$ and $\tau_3$ which are expressed by the aforementioned Equations (1) and (2). Here, the time period $\tau_0$ is that for the back edge $\alpha_0$ of the leading electrolyte ion component zone L to reach the constricted portion 7d, and the time period $\tau_3$ is that required for the ion component zone S of the sample in a conventional quantity to reach and pass through one point when it electrically migrates in the constant current $I_1$. Therefore, that time period $\tau_3$ implies that for a portion slightly upstream of the back edge of the ion component zone S of the sample to reach the constricted portion 7d. Therefore, the microcomputer 9 restores the controls of the power source circuit 2 and the switching circuit 16 after the period $\tau$ to supply the constant current $I_2$ between the terminal electrolyte chamber 3 and the first leading electrolyte chamber 4. As a result, only the portion, which is composed mainly of the ion component zone S" of the target component of a small quantity is precisely separated by the capillary tube 7b and is detected.

In the foregoing description, incidentally, the "blank start" has been conducted so as to deduce the time period $\tau_0$ and the time $t_1$. However, if it is known in advance that the conductivity of the ion component zone S' of the component of the sample other than the target is apparently lower than that of the leading electrolyte ion component zone L, the "blank start" may be omitted, and the "start of one nth" is abruptly started. Since, in this case, the microcomputer 9 is not set with the times $t_0$ and $t_1$, the time when the passage detecting means first generates its output is assumed to be $t_0$, and the time when the back edge of the leading electrolyte ion component zone L is detected by the detector 6 is assumed to be $t_1$. The remaining operations are made similar to those of the foregoing description.

According to the electrophoretic apparatus 17 thus far described, as has been described hereinbefore, the component other than the target, which occupies most of the sample, is first made as the pre-separation to migrate promptly in a large current to the tube 14 outside of the analyzing system. Next, only the portion composed mainly of the target component in a small quantity is made as the fine separation to migrate slowly in a small quantity within the capillary tube 7b so that it can be detected. As a result, the analyzing time is shortened, and the analysis itself can be conducted highly accurately. Generally speaking, the electrophoretic apparatus under consideration is remarkably useful for the electrophoretic analysis of the sample which contains the target component in a small quantity and the other components in a large quantity having a higher mobility.

Reference numeral 21 appearing in FIG. 8 indicates a further embodiment of the electrophoretic apparatus according to the present invention. The reference numerals 2-7 have the same meanings with those of FIG. 1. As has been described in connection with the foregoing embodiments, the A-D converter 12 and the microcomputer 9 constitute together passage detecting means for detecting that the boundary of ion component zones passes through the stepped portion 7c, and also the microcomputer 9 acts as the control means.

Numeral 19 indicates a branch tube which has its one end connected to the tube 7 slightly at the side of the sample injector 5 from the stepped portion 7c through a valve 18. This valve 18 is controlled by the microcomputer 9.

A plunger pump 20 acting as electrolyte injection means is connected with the other end of the aforementioned branch tube 19 and is controlled by the microcomputer 9 to inject the leading electrolyte into the tube 7.

The operations of the electrophoretic apparatus 21 thus constructed will be described in the following. For convenience of explanation, incidentally, it is assumed that the sample is composed of two kinds of ion components and that the ion components are in remarkably small quantities and have close mobilities.

If the isotachophoresis is conducted in accordance with the well-known procedures, the sample electrically migrates while being separated into two adjacent ion component zones $S_1$ and $S_2$, as shown in FIGS. 10(a) and (b). If this isotachophoresis is continued as it is, moreover, the timewise change in the supply voltage from the power source circuit 2, i.e., the first order derivative V' is substantially as illustrated in FIG. 9. Here, the times $t_0$ and $t_1$ when the first order derivative V' abruptly varies are those when the trailing end boundary of the ion component zone L of the leading electrolyte and the leading end boundary of the ion component zone T of the terminal electrolyte pass through the stepped portion 7c, respectively, and are detected by the microcomputer 9.

FIG. 10(a) schematically illustrates the state of the inside of the tube upstream and downstream of the stepped portion 7c at the time $t_0$, and FIG. 10(b) schematically illustrates the state at the time $t_1$.

The microcomputer 9 opens when it detects the unique change in the voltage at the time $t_1$, the value 18, which has been closed until that time, thereby to operate the plunger pump 20 so that the electrolyte identical to the leading electrolyte may be injected into the tube 7. This state is illustrated in FIG. 10(c). After the injection the microcomputer 9 again closes the value 18.

Moreover, if a current is further fed on and on to effect the electrophoresis, the ion zone L of the electrolyte injected catches up with the ion component zones $S_1$ and $S_2$ of the sample, which have migrated before, and the ion component zone T of the little amount of the terminal electrolyte, because the zone L of the electrolyte injected has high mobility. And then the zone L of the electrolyte injected outruns T, S, and $S_2$ while overlapping.

At this time, the ion component zones $S_1$ and $S_2$ of the sample and the ion component zone T of the terminal electrolyte electrically migrate substantially through the ions of the electrolyte L so that they are subjected to one kind of zone electrophoresis until they have their lengths enlarged and are separated from one another by the ion component zone L of the electrolyte injected.

The term of "zone electrophoresis" as used herein and hereafter means an electrophoresis which uses either one of the leading electrolyte and the terminal electrolyte, or another electrolyte in the apparatus in accordance with this invention.

As a result, the data obtained by the detector 6 are, as illustrated in FIG. 11, such that the peaks $P_1$ and $P_2$ respectively corresponding to the ion component zone $S_1$ and $S_2$ of the sample have their widthes suitably widened and are so clearly separated as are suitable for the analysis.

On the contrary, the data obtained only by the usual isotachophoresis are, as illustrated in FIG. 12, such that peaks $P_1$ and $P_2$ have excessively narrow widths and are so closely positioned that they are difficult to be sufficiently analyzed.

As has already been apparent from the description thus far made, according to the electrophoretic apparatus 21 of the present invention, the isotachophoresis is effected as the pre-separation, and one kind of zone electrophoresis is effected as the fine separation subsequent to the former. Therefore, the apparatus 21 of the invention is remarkably useful for the analysis of the sample which contains components in remarkably small quantities and having near mobilities.

Figure 13:
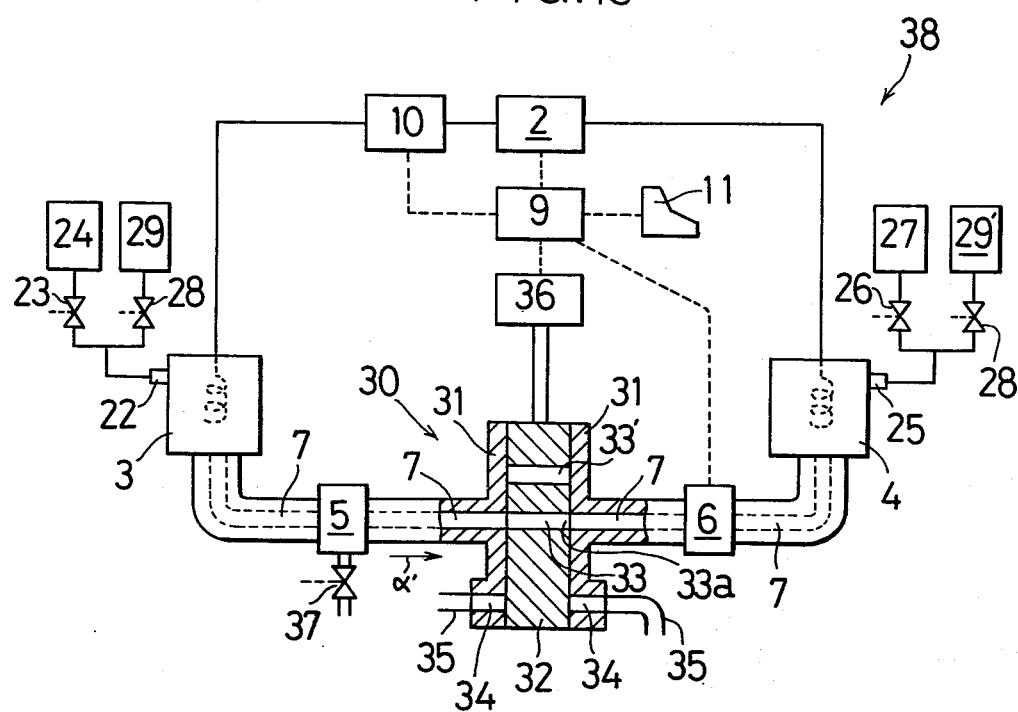
FIG. 13 is a diagram showing the construction of an electrophoretic analysis apparatus according to a further embodiment of the present invention.

Reference numeral 38 appearing in FIG. 13 indicates a further embodiment of the present invention. Like parts are indicated at reference numerals similar to those of the preceding embodiments. The passage detecting means is constituted by the current detecting circuit 10 and the microcomputer 9.

The terminal electrolyte chamber 3 is connected through a terminal electrolyte inlet 22 and a valve 23 with a terminal electrolyte tank 24, whereas the leading electrolyte chamber 4 is connected through a leading electrolyte inlet 25 and a valve 26 with a leading electrolyte tank 27. Moreover, the terminal electrolyte inlet 22 is connected through a valve 28 with an electrolyte tank 29 for zone electrophoresis, whereas the leading electrolyte inlet 25 is likewise connected through a valve 28' with an electrolyte tank 29' for zone electrophoresis. When the leading or terminal electrolyte is utilized for zone electrophoresis, the electrolyte tank 29 or 29' may be omitted.

The center portion of the tube 7 between the sample injector 5 and the detector 6 is omitted and equipped with a switching connector 30. More specifically, the omitted ends of the tube 7 are formed with sliding flanges 31, between which a sliding member 32 is interposed in a slidable manner. The sliding member 32 is formed with a communication path 33 for electrophoresis and a communication path 33' for electrolyte injection, either of which can be connected with the omitted portion of the tube 7. On the other hand, the sliding flanges 31 are partially formed with second sample injectors 34 which are different from the aforementioned sample injector 5 and with which sample injection tubes 35 are connected. By bringing the sliding members 32 into sliding movements, the communication path 33 can be connected with the second sample injectors 34.

Numeral 36 indicates a drive mechanism for the sliding member 32, which is controlled by the microcomputer 9. Thus, the microcomputer 9 and the drive mechanism 36 constitute together the control means.

Figures 14A, 14B, 14C:
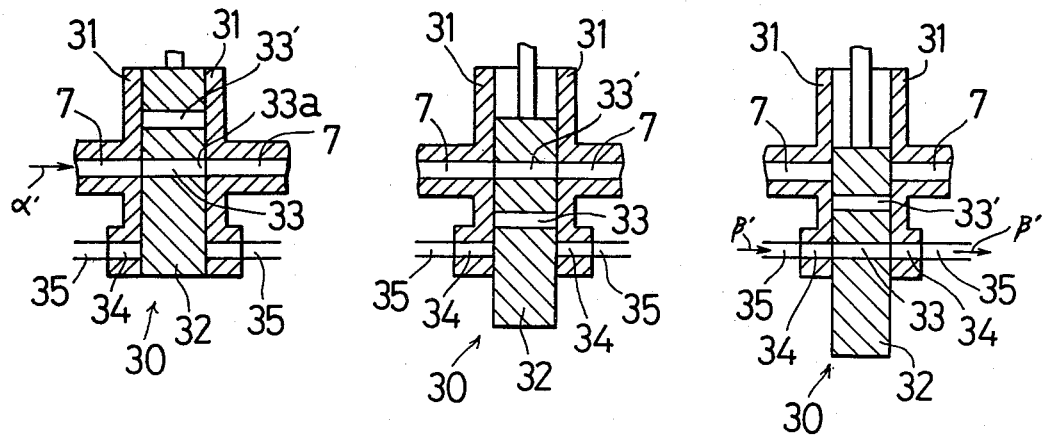
FIG. 14 is an explanatory view illustrating the respective switching positions of the communication paths of the apparatus shown in FIG. 13.

The operations of the apparatus 38 thus constructed will be described in the following. It is assumed that the omitted portion of the tube 7 is connected at the initial state with the communication path 33. First of all, the composition of the leading electrolyte is fed through the control table 11 to the microcomputer 9. Then, this microcomputer 9 reads out the corresponding quantity of electricity Q from the memory and internally sets it. Next, there is formed in the sample injector 5 by the usual procedures the boundary between the terminal and leading electrolytes, into which a sample is injected. A "link analysis start" command is fed from the control table 11. The microcomputer 9 controls the power source circuit 2, upon reception of that "link analysis start" command, to feed out the migration current thereby to start the isotachophoresis. This migration current $i_1$ is fed from the current detecting circuit 10 to the microcomputer 9, which timewise integrates the migration current $i_1$ and compares the quantity of electricity q obtained by the integration with the aforementioned quantity of electricity Q. FIGS. 13 and 14(a) show this state, at which the ion component zones electrically migrates at an equal velocity in the direction of arrow $a'$.

When the back edge of the ion component zone of the leading electrolyte reaches a path outlet 33a, the integrated quantity of electricity q coincides with the quantity of electricity Q. Then, the computer 9 operates both the power source circuit 2 to stop the migration current and the drive mechanism 36 to disconnect the communication path 33 from the migration tube 7 but to connect the communication path 33' with the migration tube 7, as shown in FIG. 14(b). As a result, in the communication path 33, there is trapped a portion of the ion component zone of the sample, which follows the ion component zone of the leading electrolyte. Subsequently, the computer 9 opens a drain cock 37 to wholly discharge the electrolytes from the tube 7 and then opens the values 28 and 28' to fill up the tube 7 with the electrolyte for zone electrophoresis. The computer 9 operates the drive mechanism 36, after it has closed the valves 37, 28 and 28', to connect the communication path 33 with the tube 7 and operates the power source circuit 2 to feed out the migration current $i_2$. The ion component zone of the sample, which has been trapped in the communication path 33, restarts its electrophoresis, which is the zone electrophoresis described before.

At last, the sample is subjected to the isotachophoresis from the sample injector 5 to the switching connector 30 and to the zone electrophoresis from that switching connector 30 to the detector 6.

Now, upon the analysis of a reference sample, a "reference sample analysis start" command is first fed from the control table 11 to the microcomputer 9. Then microcomputer 9 operates the drive mechanism 36 to locate the switching connector 30 at a position of FIG. 14(c) and informs the operator of the end of preparation for the sample injection.

Then, the operator injects the reference sample into the communication path 33, as indicated at arrow, and feeds an "end of the sample injection" from the control table 11 after filling up the communication path 33 with the reference sample.

Then, the microcomputer 9 operates the drive mechanism 36 to locate the switching connector 30 at a position of FIG. 14(b). Subsequently, the microcomputer 9 subjects the reference sample to the zone electrophoresis similarly to the aforementioned operation.

As has been understood from the foregoing description, according to the electrophoretic apparatus 38 thus constructed, the isotachophoresis and the zone electrophoresis can be easily linked, and the reference sample can be injected into a position for the start of the zone electrophoresis thereby to effect the zone electrophoresis so that the apparatus 38 can enjoy an advantage that it can directly conduct the comparison.

Since the above as well as other modifications and changes are intended to be within the scope of the present invention, the foregoing description should be construed as illustrative and not in the limiting sense, the scope of the invention being defined by the appended claims.

What is claimed is:

1. An electrophoretic apparatus of the type, in which a sample injector and a detector are connected in this order by means of a migration tube between terminal and leading electrolyte chambers connected with both the output terminals of a D.C. high voltage power source circuit, respectively, comprising:

said migration tube comprising a two-step tube including a first separation tube with a larger diameter and a second separation tube with a smaller diameter, connected in series through a stepped portion;

a passage detecting means disposed in said power source circuit for detecting that the boundary between ion component zones passes through said stepped portion; and a control means for changing the output voltage or the output current of said power source circuit in accordance with the output signal of said passage detecting means, whereby a rough separation and a subsequent fine separation can be effected in the migration tube.

2. An electrophoretic apparatus according to claim 1, wherein said control means is a change means for supplying said migration tube at first with a relatively high constant voltage or current to effect said rough separation and thereafter with a relatively low constant current in accordance with the output of said passage detecting means to effect said fine separation.

3. An electrophoretic apparatus according to claim 1, wherein the internal diameter of said first separation tube is 0.8 to 1.2 mm whereas the internal diameter of said second separation tube is 0.1 to 0.5 mm.

4. An electrophoretic apparatus in which a sample injector and a detector are connected in this order by means of a migration tube between terminal and leading electrolyte chambers connected with both the output terminals of a D.C. high voltage power source circuit, respectively, comprising:
   said leading electrolyte chamber including a first leading electrolyte chamber and a second leading electrolyte chamber; said sample injector and said detector connected in this order by said migration tube between said terminal electrolyte chamber and said first leading electrolyte chamber; said migration tube between said sample injector and said detector comprising a two-step tube including a first separation tube with a larger diameter and a second separation tube with a smaller diameter connected in series through a stepped portion,
   a branch tube connected to said first separation tube and having said larger diameter and said branch tube located adjacent to said stepped portion and connected to said second leading electrolyte chamber;
   a passage detecting means disposed in said power source circuit for detecting that the boundary between ion component zones passes through the stepped portion; and
   a control means for changing the output voltage or output current of said power souce circuit in accordance with the output signal of said passage detecting means, whereby a rough separation can be effected in the migration tube between the terminal electrolyte chamber and the second leading electrolyte chamber, and a subsequent fine separation can be effected in the migration tube between the terminal electrolyte chamber and the first leading electrolyte chamber.

5. An electrophoretic apparatus according to claim 4, wherein said control means is switch means for supplying the tube portion between said terminal electrolyte chamber and said second leading electrolyte chamber at first with a relatively high constant voltage or current to effect said rough-separation and said migration tube between said terminal electrolyte chamber and said first leading electrolyte chamber thereafter with a relatively low constant current in accordance with the output of said passage detecting means to effect said fine separation.

6. An electrophoretic apparatus according to claim 1 or 5, wherein said apparatus further comprises the following means (i), (ii) and (iii):
   (i) means for measuring and storing both the time period $\tau_0$, for which the back edge of the ion component zone of the leading electrolyte electrically migrates in a relatively high constant current $I_1$ from said sample injector to said predetermined position, and the time period $\tau_1$, for which said back edge electrically migrates in a relatively low constant current $I_2$ from said predetermined position to said detector, in accordance with the output signal of said passage detecting means;
   (ii) means for measuring and storing the time period $\tau_2$ from the instant when said constant current $I_2$ begins to be supplied to the instant when said detector detects the front edge of the ion component zone of the terminal electrolyte, with a proviso that a sample in one nth of a conventional quantity is subjected to the electrophoresis under the constant current $I_1$, for the period $\tau_0$ and subsequent electophoresis under the constant current $I_2$; and
   (iii) means for conducting such a calculation by the use of a suitable safety factor smaller than 1 as is defined in the following equation:

$$\tau = C \times [\tau_0 + (\tau_2 - \tau_1) \times n \times (I_2/I_1)];$$

whereby said control means supplies said constant current $I_1$ as said relatively high constant current for a time period $\tau$ at first, when a sample in said conventional quantity is injected, to effect said rough-separation and supplies thereafter said constant current $I_2$ as said relatively low constant current to effect said fine separation.

7. An electrophoretic apparatus of the type, in which a sample injector and a detector are connected in this order by means of a migration tube between terminal and leading electrolyte chambers connected with both the output terminals of a D.C. high voltage power source circuit, respectively, comprising:
   a passage detecting means for detecting that the boundary between ion component zones passes through a predetermined position of said migration tube between said sample injector and said detector;
   a branch tube connected to a tube portion in the vicinity of said predetermined position between said predetermined position and said sample injector;
   an electrolyte injection means connected with said branch tube; and
   a control means for operating said electrolyte injection means in accordance with the output signal of said passage detecting means,
   whereby a rough separation can be effected in the migration tube by using both said leading and terminal electrolytes, and a subsequent fine separation can be effected in said migration tube by using either one of said two electrolytes or another electrolyte.

8. An electrophoretic apparatus according to claim 7, wherein said electrolyte is the same as the leading electrolyte.

9. An electrophoretic apparatus of the type, in which a sample injector and a detector are connected in this order by means of a migration tube between terminal and leading electrolyte chambers connected with both the output terminals of a D.C. high voltage power source circuit, respectively, comprising:
   a passage detecting means for detecting that the boundary between ion component zones passes through a predetermined position of said migration tube between said sample injector and said detector;
   said passage detecting means provided with a current detecting means for detecting the migration current which is supplied from said power source circuit, a current integrating means for timewise integrating the currents detected and a comparison means for comparing the integrated value with a predetermined threshold value;

a switching connection means disposed in said predetermined position and having a communication path for migration and a communication path for electrolyte injection, aribtrary one of which is switched to be connected with said migration tube; and a control means for switching said switching connection means in accordance with output signal of said comparison means of said passage detecting means, whereby a rough separation can be effected in the migration tube by using both said leading and terminal electrolytes, and a subsequent fine separation can be effected in said migration tube by using either one of said two electrolytes or another electrolyte.

10. An electrophoretic apparatus according to any of the claim 1 or 4, wherein said passage detecting means comprises: current detecting means for detecting the migration current which is supplied from said power source circuit; current integrating means for timewise integrating the currents detected; and comparison means for comparing the integrated value with a predetermined threshold value, wherein said threshold value is present at an integrated value which is integrated until the back edge of a leading electrolyte ion component zone reaches said stepped position of said migration tube.

11. An electrophoretic apparatus according to claim 8, wherein said passage detecting means comprises: current detecting means for detecting the migration current which is supplied from said power source circuit; current integrating means for timewise integrating the currents detected; and comparison means for comparing the integrated value with a predetermined threshold value, and wherein said threshold value is present at an integrated value which is integrated until the back edge of a leading electrolyte ion component zone reaches said predetermined position of said migration tube.

12. An electrophoretic apparatus according to any of the claims 1, 4, 7 or 9, wherein said passage detecting means comprises: voltage change measuring means connected with said power source circuit for measuring the timewise change in the voltage supplied; and comparison means for comparing the change in the voltage measured with a predetermined threshold value.

* * * * *

UNITED STATES PATENT AND TRADEMARK OFFICE
CERTIFICATE OF CORRECTION

PATENT NO. : 4,459,198
DATED : July 10, 1984
INVENTOR(S) : Toshie Mizumo and Stoichi Kobayashi It is certified that error appears in the above-identified patent and that said Letters Patent is hereby corrected as shown below:

Column 6, Line 19: "compartment" should read --component--

Column 12, Line 39: "widthes" should read --widths--

Signed and Sealed this

Fifteenth Day of July 1986

[SEAL]

Attest:

DONALD J. QUIGG

Attesting Officer

Commissioner of Patents and Trademarks